United States Patent [19]

Takeda et al.

[11] 4,435,251

[45] Mar. 6, 1984

[54] METHOD FOR PURIFICATION OF 2-METHYLENEGLUTARONITRILE

[75] Inventors: Makoto Takeda; Kazuhito Miyoshi, both of Ami; Mitsumasa Kaitoh, Kashiwa; Hiroyuki Omori, Yokkaichi, all of Japan

[73] Assignee: Mitsubishi Petrochemical Company Limited, Tokyo, Japan

[21] Appl. No.: 334,815

[22] Filed: Dec. 28, 1981

[30] Foreign Application Priority Data

Dec. 27, 1980 [JP] Japan .................................. 55-185497

[51] Int. Cl.³ .............................................. B01D 3/34
[52] U.S. Cl. ....................................... 203/50; 203/77; 203/81; 203/91; 260/465.8 R; 260/465.8 D
[58] Field of Search ................. 260/465.8 R, 465.8 D; 203/50, 77, 81, 91

[56] References Cited

U.S. PATENT DOCUMENTS

| | | |
|---|---|---|
| 2,920,099 | 1/1960 | Ringwald ...................... 260/465.8 R |
| 3,206,497 | 9/1965 | Oblad ....................... 260/465.8 R X |
| 3,446,836 | 5/1969 | Lambert et al. ............. 260/465.8 D |
| 3,567,759 | 3/1971 | Tullio ........................ 260/465.8 D |
| 3,733,351 | 5/1973 | Watanabe et al. ........... 260/465.8 D |
| 4,146,555 | 3/1979 | Kershaw ..................... 260/465.8 R |

FOREIGN PATENT DOCUMENTS

| | | |
|---|---|---|
| 713592 | 7/1965 | Canada ......................... 260/465.8 R |
| 1283823 | 11/1968 | Fed. Rep. of Germany ... 260/465.8 |
| 2131448 | 12/1971 | Fed. Rep. of Germany ... 260/465.8 |
| 322323 | 3/1969 | German Democratic Rep. ............................ 260/465.8 R |
| 47-06290 | 2/1972 | Japan .......................... 260/465.8 R |
| 731458 | 6/1955 | United Kingdom ............ 260/465.8 |

OTHER PUBLICATIONS

Perry and Weissberger, Techniques of Organic Chemistry, vol. IV, Distillation (2nd Ed.), 1965, pp. 511-513.

*Primary Examiner*—Joseph P. Brust
*Attorney, Agent, or Firm*—Oblon, Fisher, Spivak, McClelland & Maier

[57] ABSTRACT

Crude 2-methyleneglutaronitrile containing as impurities a metal halide, a trialkylamine, and the trimer or a higher polymer of acrylonitrile can be effectively purified by treating the crude 2-methyleneglutaronitrile with hydrochloric acid, sulfuric acid or nitric acid of a concentration of 1 to 30% by weight and then subjecting the treated methyleneglutaronitrile to vacuum distillation.

3 Claims, No Drawings

METHOD FOR PURIFICATION OF 2-METHYLENEGLUTARONITRILE

BACKGROUND OF THE INVENTION

1. Field of the Invention

This invention relates to a method for purification of 2-methyleneglutaronitrile (hereinafter sometimes referred to as MGN).

MGN is an important chemical to be used as an intermediate for pharmaceuticals, agricultural chemicals and various polymers. Accordingly, various methods for preparation thereof have heretofore been developed.

Of these methods for preparation, a method of dimerizing acrylonitrile in the presence of a catalyst composed of a metal halide and a trialkylamine as disclosed in U.S. Pat. No. 3,733,351 is an excellent method.

A distillation method may be thought to be suitable for recovering the objective MGN from the reaction product obtained by the above mentioned method. It has been found, however, that there exist, unexpectedly, various technical problems in the recovery and purification by distillation of MGN in commercial production. For example, the reaction product contains the metal halide used as the catalyst, and the metal halide accelerates polymerization of MGN when the reaction product is distilled at a temperature of about 100° C. or higher, thereby lowering the yield of MGN. Moreover the polymerization reaction progresses explosively and is dangerous. Further, in the above-mentioned reaction of acrylonitrile, a portion of the trialkylamine used as the catalyst and the metal halide form an adduct, which is fixed in the reaction product. The adduct is gradually decomposed in the course of the distillation and the trialkylamine thus yielded goes as an impurity into the distillate MGN. No prior art references dealing with commercial purification of MGN have been found.

2. Possible Solution of the Problems

We had found that the problems encountered in the case of recovering MGN from such crude MGN can be solved by pretreating the crude MGN with an alkali. According to this method, the metal halide is converted into the corresponding hydroxide and is separated out in the crude MGN liquid to lose its catalytic action. On the other hand, the adduct of the trialkylamine and the metal halide is decomposed, and the trialkylamine thus yielded is also driven out of the alkaline crude MGN liquid. Although some of the trialkylamine may still remain in the crude MGN, it can be trapped as a low-boiling substance in an initial distillate fraction in the course of the distillation. Thus, the above mentioned problems observed in the direct distillation of crude MGN can be solved.

It has been found, however, that there still remain some problems in this method. That is, the metal hydroxide formed by the alkali treatment is separated out as very fine particles, and the particles are difficult to remove. Moreover, in the distillation of the alkali-treated MGN, MGN is apt to polymerize because of a slight amount of the alkali present.

SUMMARY OF THE INVENTION

An object of this invention is to solve the above mentioned problems in the recovery by distillation of 2-methyleneglutaronitrile, which is accomplished by using an acid treatment jointly with the above mentioned method for purification.

The method for purifying 2-methyleneglutaronitrile according to the present invention is characterized by the steps of treating with hydrochloric acid, sulfuric acid or nitric acid of a concentration of 1 to 30% by weight the crude 2-methyleneglutaronitrile containing as impurities a metal halide, a trialkylamine and trimer or a higher polymer of acrylonitrile, and then subjecting the treated material to distillation under a reduced pressure.

In accordance with the present invention, both the recovery of MGN by the direct distillation of crude MGN and the problems encountered in the pretreatment of the crude MGN have been solved by a very simple measure, that is, the acid pretreatment of the crude MGN. More specifically, the following advantages are attained by the acid treatment of the present invention.

(1) No separation of very fine particles of metal hydroxides is observed. Metal halides can be removed readily.

(2) The free trialkylamine resulting from the decomposition of an adduct of the trialkylamine and the metal halide forms an adduct thereof with the treating acid and is removed into the water layer. It does not easily mix into purified MGN.

(3) Even if the acid is partly mixed into the MGN to be distilled, polymerization of the MGN as in the case of the alkali treatment will not easily take place.

We have thus developed the present invention on the basis of our discovery that by the present method which comprises washing with an acid, which may seem to be an easy measure, and then recovering MGN by distillation, unexpected advantages with respect to the distilling operation as well as the yield and purity of the MGN are obtainable.

DETAILED DESCRIPTION OF THE INVENTION

Crude MGN to be treated

Crude MGN to be treated in the present invention is such that it contains a metal halide, a trialkylamine, and trimer or a higher polymer of acrylonitrile.

Such a crude MGN is typically represented by a reaction product obtained by dimerizing acrylonitrile in the presence of a catalyst comprising a metal halide and a trialkylamine and the above-mentioned reaction product which has been treated by distilling off some low-boiling impurities, that is, at least a portion of and preferably substantially all of acrylonitrile and a portion of the trialkylamine. Of these, the latter, namely the reaction product from which the low-boiling impurity has been removed is preferable. As described above, the trialkylamine is present in the form of an adduct with the metal halide and is not easily distilled off, whereby the crude MGN from which such low-boiling impurities have been distilled off generally contains a significant quantity (for example, 1 to 5% by weight) of the trialkylamine.

Since the purpose of the pre-distillation for obtaining this preferred crude MGN is to distill off the low-boiling impurities, it does not require such a high temperature as in the distillation of MGN. Thus, such problems as those encountered in the direct distillation of crude MGN do not arise in the pre-distillation. The pre-distillation is preferably carried out under a reduced pressure of 10 to 200 mmHg at a temperature of not higher than about 120° C. and preferably about 10° to about 90° C.

The dimerization reaction of acrylonitrile in the presence of a metal halide/trialkylamine catalyst has been known, and thus the resulting reaction product has also been known. The details concerning this dimerization reaction are set forth in the aforecited U.S. Pat. No. 3,733,351, but particulars which are significant as to the relationship of this reaction with this invention will now be described.

The metal halide is represented by the formula $MeX_n$, wherein Me stands for aluminum, titanium, vanadium, iron, cobalt or zinc; X is a halogen; and n is equivalent to a valence of the metal Me. The trialkylamine is represented by the formula $NR^1R^2R^3$, wherein each of $R^1$, $R^2$ and $R^3$ stands for an alkyl group and especially an alkyl group having 1 to about 8 carbon atoms, two or three of which may be bonded to each other and form a nitrogen-containing ring. Thus, in the term "trialkylamine" used herein, the alkyl includes alkylene groups forming such a nitrogen-containing ring. This dimerization reaction may be conducted in the presence of a solvent or a dispersion medium but is ordinarily carried out in the absence of a solvent.

Acid-Treatment

The acid for pretreating the crude MGN in accordance with the present invention is hydrochloric acid, sulfuric acid or nitric acid. These acids should be in a relatively low concentration (an aqueous solution), that is, a concentration of 1 to 30% by weight. When the concentration is lower than 1%, a large volume of the aqueous acid solution must be used, and it also becomes difficult to separate the solution from a crude MGN having a specific gravity of about 1. In the case of a concentration higher than 30%, the solubility of MGN in the aqueous solution is increased, and moreover the yield is apt to be lowered because of the reaction of a part of MGN. The above range of concentration is thus defined. The term "a concentration of 1 to 30% by weight" used herein includes the case where the acid of a concentration of 1 to 30% is added into the crude MGN, as well as the case where the acid of a higher concentration and water are introduced into the crude MGN, whereby the acid having the desired concentration is formed in situ.

The quantity of the acid to be used is optional provided that the desired effect is achieved under the given conditions. In general, it is preferred to use 1 equivalent or more of the acid and especially 1 to about 5 equivalents of the acid relative to the total quantity of the metal halide and the trialkylamine contained in the crude MGN.

The acid-treatment can be applied to the crude MGN alone, but it is preferably carried out in the presence of a substantially water-immiscible organic solvent for MGN. By the action of the solvent, the distribution of MGN into an organic phase and the distribution of the metal halide into an aqueous phase become advantageous. The solvent to be used should be inactive to MGN and the acid, and also the MGN must have a high solubility therein. The most typical examples of the solvent are aromatic hydrocarbons such as benzene, toluene, ethylbenzene and xylene. The quantity of the solvent used is preferably in the range of 0.1 to 2 volumes and more preferably 0.2 to 1 volume relative to that of the crude MGN.

The acid-treatment can be carried out by an any suitable procedure which can realize sufficient contact of the aqueous acid with the oily crude MGN or a solution thereof. In general, it is preferred to carry out the treatment by subjecting a mixture of these components to shaking, stirring, or other liquid/liquid contacting measure. The treating temperature is preferably at value of the order of about 70° C. or lower, especially about 10° to about 50° C. The treating time is generally in the range of 1 to about 30 minutes.

After the acid-treatment, the crude MGN may be directly subjected to distillation as it is, but it is preferred to subject the oily layer obtained by removing an aqueous layer from the crude MGN to the distillation. More preferably, before the distillation step, the aqueous layer is separated from the crude MGN, and then the resulting oily layer is washed with water or a dilute alkali solution to remove or neutralize the acid dissolved in the oily layer. The alkali to be used is preferably an inorganic basic compound such as sodium hydroxide, sodium carbonate, or sodium hydrogen carbonate. Also in this case, it is preferable that the water or aqueous alkali solution to be used for the washing contain a suitable concentration (e.g., about 5 to 20% by weight) of an inorganic salt dissolved therein inactive to MGN such as sodium chloride and sodium sulfate, in order to make the difference in specific gravity with respect to the oily layer greater thereby to facilitate the separation from the oily layer. In washing with an aqueous alkali solution, care should be taken not to make the oily layer alkaline.

Distillation

The distillation to recover MGN from the crude MGN thus pretreated is preferably carried out under a reduced pressure, especially under a pressure of 0.1 to 30 mmHg, and at a temperature at which MGN is distilled under the pressure used, e.g., about 70° to about 160° C. At a temperature over 160° C., it is observed that MGN is apt to polymerize.

Preferably, the distillation is carried out by adding to the crude MGN solution 0.001 to 1%, preferably 0.005 to 0.5%, by weight of a polymerization inhibitor such as hydroquinone, p-methoxyphenol, p-nitrophenol, or phenothiazine.

The resulting MGN is obtained with a high purity of 99.8% or higher, which contains almost no trialkylamines.

Experimental Examples

EXAMPLE 1

Four hundred (400)g of acrylonitrile, 80 g of triethylamine and 20 g of zinc chloride were caused to react at 25° to 30° C. for 24 hours. Triethylamine and unreacted acrylonitrile were distilled off from the resulting reaction mixture under a reduced pressure of 70 to 150 mmHg and at a temperature of 25° to 50° C. Thus 410 g of crude MGN was obtained. The crude MGN was found to consist of 80% of MGN, 5% of triethylamine and balance of other impurities as a result of gas-chromatographic analysis, the impurities being mainly the trimer or a higher polymer of acrylonitrile and zinc chloride.

Two hundred (200)g of toluene and then 85 g of 25% sulfuric acid were added to 410 g of this crude MGN. The mixture was thoroughly stirred and allowed to stand. After stratification, the lower aqueous layer was drained off. The resulting organic layer was washed with 50 g of an aqueous solution containing 3% of sodium hydroxide and 15% of sodium sulfate and then with 100 g of an aqueous solution containing 15% of sodium sulfate.

Five hundred and fifty (550)g of the resulting oil layer was subjected to distillation under a reduced pressure, whereupon 305 g of the MGN fraction at 122° to 124° C. was obtained under a pressure of 9 to 10 mmHg. The purity of the resulting MGN was 99.9%.

EXAMPLE 2

Example 1 was repeated except that 80 g of 20% hydrochloric acid was used instead of 85 g of 25% sulfuric acid, to obtain 302 g of MGN having a purity of 99.9%.

EXAMPLE 3

Example 1 was repeated except that 135 g of 20% nitric acid was used instead of 85 g of 25% sulfuric acid, to obtain 300 g of MGN having a purity of 99.9%.

What is claimed is:

1. In a method for purification of crude 2-methyleneglutaronitrile product containing as impurities a metal halide, a trialkylamine, and a trimer or higher polymer of acrylonitrile, which crude product is a reaction product obtained by dimerizing acrylonitrile in the presence of a catalyst comprising a metal halide and a trialkylamine, wherein the purification comprises treating said crude 2-methyleneglutaronitrile product with an acid and then subjecting the treated product to distillation, the improvement comprising effecting said purification by the following sequential steps:
    (1) subjecting said reaction product to predistillation at a temperature of 120° C. or lower under a pressure of 10 to 200 mm Hg to distill off therefrom at least portions of unreacted acrylonitrile and trialkylamine;
    (2) treating said crude 2-methyleneglutaronitrile product with an acid selected from the group consisting of hydrochloric acid, sulfuric acid and nitric acid of a concentration of 1 to 30% by weight at a temperature of 10° to 50° C. in the presence of an aromatic hydrocarbon selected from the group consisting of benzene, toluene, ethylbenzene and xylene in a quantity of 0.1 to 2 volumes relative to that of the crude 2-methyleneglutaronitrile;
    (3) separating the acid-treated crude product from the aqueous layer, and washing the remaining organic layer with a dilute aqueous alkaline solution; and
    (4) subjecting the washed crude product to distillation under a reduced pressure.

2. The method according to claim 1, in which the distillation is carried out at a temperature of 70° to 160° C. under a pressure of 0.1 to 30 mmHg.

3. The method according to claim 1, in which the acid treatment is conducted in the presence of a substantially water-immiscible solvent for 2-methyleneglutaronitrile.

* * * * *